(12) United States Patent
Miller et al.

(10) Patent No.: US 10,137,428 B2
(45) Date of Patent: Nov. 27, 2018

(54) ZEOLITE PARTICLES FOR ADSORPTION AND/OR DESORPTION OF GASES AND LIQUIDS

(71) Applicant: W. R. Grace & Co.-Conn., Columbia, MD (US)

(72) Inventors: James George Miller, Ellicott City, MD (US); Robert Harding, Woodstock, MD (US); Demetrius Michos, Clarksville, MD (US); James Neil Pryor, West Friendship, MD (US)

(73) Assignee: W. R. GRACE & CO.-CONN, Columbia, MD (US)

( * ) Notice: Subject to any disclaimer, the term of this patent is extended or adjusted under 35 U.S.C. 154(b) by 0 days.

(21) Appl. No.: 15/302,413

(22) PCT Filed: Apr. 8, 2015

(86) PCT No.: PCT/US2015/024939
§ 371 (c)(1),
(2) Date: Oct. 6, 2016

(87) PCT Pub. No.: WO2015/157429
PCT Pub. Date: Oct. 15, 2015

(65) Prior Publication Data
US 2017/0043318 A1 Feb. 16, 2017

Related U.S. Application Data

(60) Provisional application No. 61/977,550, filed on Apr. 9, 2014.

(51) Int. Cl.
*A23L 2/54* (2006.01)
*A23L 2/80* (2006.01)
(Continued)

(52) U.S. Cl.
CPC .................. *B01J 20/18* (2013.01); *A23L 2/54* (2013.01); *A23L 2/80* (2013.01); *A61M 16/107* (2014.02);
(Continued)

(58) Field of Classification Search
None
See application file for complete search history.

(56) References Cited

U.S. PATENT DOCUMENTS

| 3,649,556 A | 3/1972 | Hoffman .................. 252/313 S |
| 4,025,655 A | 5/1977 | Whyte et al. .................. 426/66 |

(Continued)

OTHER PUBLICATIONS

Hersh, Charles "Molecular Sieves" Reinhold Publishing Corporation (1961).
(Continued)

*Primary Examiner* — Colin W. Slifka
(74) *Attorney, Agent, or Firm* — Charles A. Cross; Beverly J. Artale

(57) ABSTRACT

Disclosed are silica bound zeolite adsorbent particles which possess high volumetric gas adsorption capacity for the adsorption and/or desorption of gases. The adsorbent are highly effective as a gas source in volumetrically constrained applications. The silica-bound zeolite adsorbents possess a relatively high zeolite content simultaneously with a relatively low intra-particle pore volume as compared to the clay bound zeolite aggregates heretofore used as a gas source in volumetrically constrained environments, e.g. instant beverage carbonation processes, devices or systems.

23 Claims, 1 Drawing Sheet

(51) Int. Cl.
*A61M 16/10* (2006.01)
*B01J 20/10* (2006.01)
*B01J 20/18* (2006.01)
*B01J 20/28* (2006.01)
*B01J 20/30* (2006.01)
*C01B 31/20* (2006.01)

(52) U.S. Cl.
CPC .......... *B01J 20/103* (2013.01); *B01J 20/183* (2013.01); *B01J 20/2803* (2013.01); *B01J 20/28004* (2013.01); *B01J 20/28011* (2013.01); *B01J 20/28016* (2013.01); *B01J 20/28019* (2013.01); *B01J 20/28071* (2013.01); *B01J 20/3007* (2013.01); *B01J 20/3028* (2013.01); *B01J 20/3035* (2013.01); *B01J 20/3042* (2013.01); *B01J 20/3078* (2013.01); *B01J 20/3092* (2013.01); *C01B 31/20* (2013.01); *A23V 2002/00* (2013.01)

(56) References Cited

U.S. PATENT DOCUMENTS

| | | | |
|---|---|---|---|
| 4,110,255 A | 8/1978 | Liepa et al. | 252/455 |
| 4,147,808 A | 4/1979 | Liepa et al. | 426/477 |
| 4,345,511 A | 8/1982 | Lunt et al. | 99/276 |
| 4,582,815 A | 4/1986 | Bowes | 502/64 |
| 4,853,355 A | 8/1989 | Behan et al. | 502/64 |
| 5,106,803 A | 4/1992 | Mohr et al. | 502/66 |
| 5,120,693 A | 6/1992 | Connolly et al. | 502/64 |
| 5,182,242 A | 1/1993 | Marler et al. | 502/66 |
| 5,460,796 A | 10/1995 | Verduijn et al. | 423/700 |
| 5,665,325 A | 9/1997 | Verduijn et al. | 423/709 |
| 5,855,863 A | 1/1999 | Verduijn et al. | 423/700 |
| 6,051,051 A | 4/2000 | Hees et al. | 95/96 |
| 6,376,730 B1 | 4/2002 | Jan et al. | 585/467 |
| 6,548,439 B2 | 4/2003 | Wu et al. | 502/64 |
| 6,841,510 B2 | 1/2005 | Vaughn et al. | 502/214 |
| 6,916,757 B2 | 7/2005 | Ziebarth et al. | 502/87 |
| 7,160,830 B2 | 1/2007 | Van Der Zon et al. | 502/8 |
| 7,384,887 B2 | 8/2008 | Chang et al. | 502/214 |
| 7,541,508 B2 | 6/2009 | Vaughn et al. | 565/640 |
| 7,572,749 B2 | 8/2009 | Beeckman et al. | 502/60 |
| 7,951,304 B2 | 5/2011 | Stueven et al. | 252/194 |
| 8,092,903 B2 | 1/2012 | Stach et al. | 428/305.5 |
| 8,123,835 B2 | 2/2012 | Zheng et al. | 95/90 |
| 2001/0008868 A1 | 7/2001 | Carati et al. | 502/54 |
| 2001/0045160 A1* | 11/2001 | Hirano | B01D 53/02 95/96 |
| 2002/0134240 A1* | 9/2002 | Zhong | B01D 53/047 95/96 |
| 2002/0140138 A1 | 10/2002 | Wu et al. | 264/630 |
| 2003/0083190 A1 | 5/2003 | Carati et al. | 502/64 |
| 2007/0100187 A1 | 5/2007 | Chang | 585/639 |
| 2008/0282887 A1 | 11/2008 | Chance et al. | 95/98 |
| 2009/0005600 A1 | 1/2009 | Bosch et al. | 564/474 |
| 2009/0071481 A1 | 3/2009 | Fishman | 128/204.18 |
| 2010/0116134 A1 | 5/2010 | Zheng et al. | 95/90 |
| 2011/0105770 A1 | 5/2011 | Liu et al. | 549/490 |
| 2011/0226343 A1 | 9/2011 | Novak et al. | 137/12.5 |
| 2012/0071614 A1 | 3/2012 | Schmidt et al. | 526/108 |
| 2012/0190900 A1 | 7/2012 | Weston et al. | 568/916 |
| 2013/0129870 A1 | 5/2013 | Novak et al. | |
| 2013/0298769 A1 | 11/2013 | Petruska et al. | B01J 20/20 |
| 2013/0340615 A1 | 12/2013 | Barrett et al. | B01J 20/26 |

OTHER PUBLICATIONS

Thomas, T. and Mays, R "Separations with Molecular Sieves" Physical Methods in Chemical Analysis, vol. IV, edited by Berl, W., Academic Press, p. 45-97 (1961).

PCT Search Report and Written Opinion for PCT/US2015/024939; dated Jul. 29, 2015.

* cited by examiner

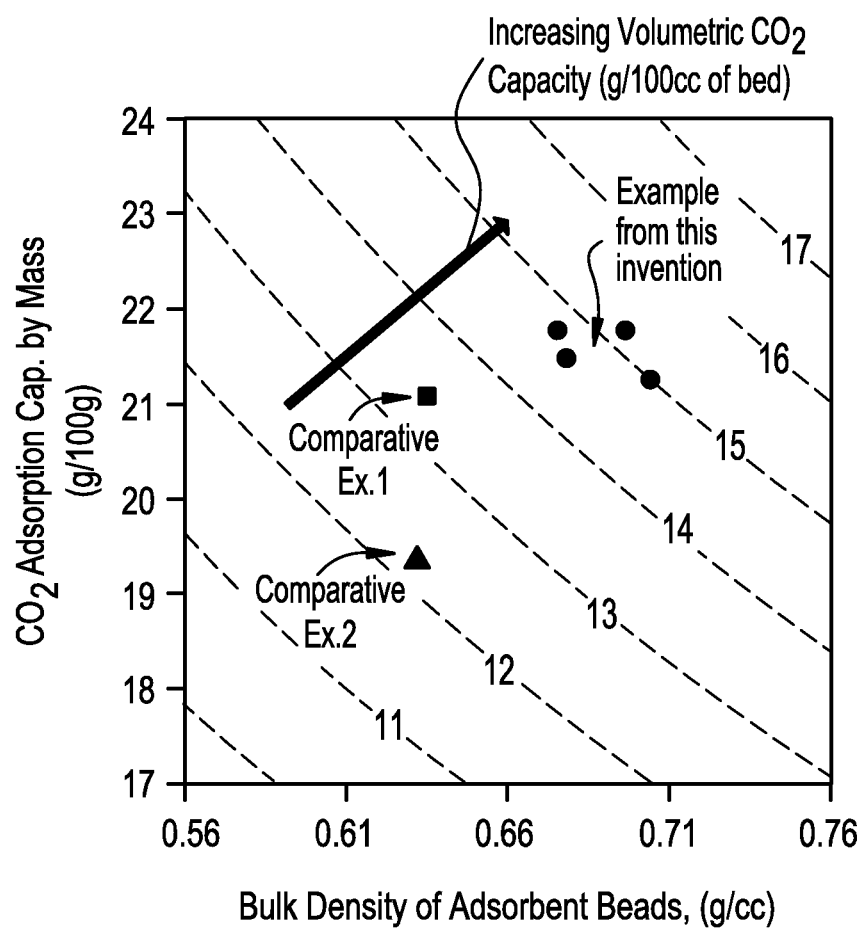

ZEOLITE PARTICLES FOR ADSORPTION AND/OR DESORPTION OF GASES AND LIQUIDS

FIELD OF THE INVENTION

This invention relates to adsorbent compositions, method of making and method of using the adsorbents. In particular, the present invention relates to novel zeolitic adsorbent compositions, method of preparing the adsorbents and the method of use thereof as a gas source in various methods, devices and systems.

BACKGROUND OF THE INVENTION

Formed zeolite bodies have been manufactured for use in various adsorption/desorption applications including drying of gases and liquids, separation of air into purified nitrogen and oxygen, and removal of CO2 from various gases.

In some applications where the controlled delivery of a small volume of gas is desired, zeolite adsorbent bodies having a desired gas adsorbed thereon have also been used as a source for delivery of gas. For example, in the instant carbonation of a beverage, zeolite adsorbent particles, typically $CO_2$ preloaded 13X zeolite clay bound particles, have been used as a source of CO2 (see for e.g. U.S. Pat. Nos. 4,025,655 and; 4,147,808; and U.S. Patent Publications US 2011/0226343 A1 and US2013/0129870). In such applications, zeolite CO2 loaded particles are contacted with a displacement fluid, e.g. water, to release CO2. The liberated CO2 is then dissolved into a potable liquid to become a constituent of a carbonated beverage. In such applications, it is important for the adsorbents to have high gas adsorption capacity and gas desorption rates.

In addition to possessing the required adsorptive properties, adsorbent particles used as a gas source must also possess a sufficient attrition resistance to withstand the physical stresses associated with both transportation and use of the product in the desired application without undue particle breakage and dust formation. Gas loaded adsorbent particles may also be subjected to volumetric restraints due to limitations caused by packaging volume. This can adversely limit the amount of the desired gas available, thereby leading to a less efficient process and an undesirable product.

Further, in certain applications where a zeolite based adsorbent is used as a gas source, the adsorbent particles may be subjected to atypically harsh physical conditions, such as for example, in the instant carbonation of a beverage or in the delivery of medical gases, e.g. anesthesia gas, in single dose units (See U.S. Patent Pub. 2009/0071481). This is due to the physical wetting of the particles coupled with the rapid heating of the particles due to heat of adsorption effects and high gas pressures within the particles due to the very rapid desorption of gas. However, the acceptable level of particle breakage and attrition in these processes can be extremely low due to the extreme sensitivity of any contamination caused by dust or fines zeolite or binder particles in the final products of these process, e.g. contamination of the consumable beverage or of the inhalation gas. Prevention of the fouling of valves or other small orifices associated with apparati used in these processes is also critical.

Another volume constrained application where the delivery of a small amount of gas is desirable, include, for example, wine making procedures wherein the introduction of controlled amount of sulfur dioxide is released into must to reduce oxidation and inhibit the growth of wild yeast residing in the must application (See U.S. Pat. No. 4,345,511).

Accordingly, there is a need in various industries to provide improved adsorbent compositions and processes which are effective, efficient and productive to provide a gas source in volumetrically constrained applications.

SUMMARY OF THE INVENTION

It has now been discovered that certain silica bound zeolite adsorbent particles unexpectedly possess an enhanced volumetric gas adsorption capacity for the adsorption and/or desorption of gases, enabling the particles to be highly effective as a gas source in volumetrically constrained applications. The silica-bound zeolite adsorbents possess a relatively high zeolite content simultaneously with a relatively low intra-particle pore volume as compared to the clay bound zeolite aggregates heretofore used as a gas source in volumetrically constrained environments, e.g. instant beverage carbonation processes, devices or systems. Advantageously, the high zeolite content promotes a high volumetric gas loading of zeolite crystals per unit volume of adsorbent, while the low intra-particle pore volume supports a rapid desorption rate when an adsorbed gas is desorbed by addition of a displacement fluid, e.g. water.

In an embodiment, the present invention provides silica bound zeolite adsorbent particles having an increased volumetric gas adsorption capacity as compared to clay bound zeolite adsorbents.

In another embodiment, the present invention provides silica bound zeolite adsorbent particles having an increased volumetric gas adsorption capacity as compared to clay bound zeolite adsorbent and an gas desorption rate equal to or greater than clay bound zeolite adsorbents.

In another embodiment, the present invention provides zeolite adsorbent particles having increased volumetric capacity for the adsorption of gas (e.g. CO2, N2, Xe, Sevoflurane, etc. . . . ) and comparable gas desorption capacity at a given volume when compared to clay bound zeolite adsorbents.

In an exemplary embodiment, the present invention provides zeolite adsorbent particles having a specified combination of high zeolite to binder content and low intra-particle pore volume to maximize gas adsorption capacity per unit volume.

In another embodiment, the present invention provides zeolite adsorbent particles having high volumetric gas adsorption capacity and good gas desorption rate simultaneously with high crush strength and good attrition resistance. The invention adsorbent particles exhibit excellent resistant to breakage and dust formation during shipping and handling as compared to zeolite adsorbent particles bound with clay binder.

In another exemplary embodiment, the present invention provides zeolite adsorbent particles having a high volumetric gas adsorption capacity for loading gas, e.g. CO2, N2, Xe, Sevoflurane, etc. . . . , in which the particles exhibit improved activity as a gas source in volumetrically constrained environments while minimizing attrition and dust formation under harsh physical conditions which may be associated with such environments.

In another exemplary embodiment, the present invention comprises silica bound zeolite adsorbent particles, wherein the zeolite adsorbent particles have a mean diameter of at least about 800 microns, a binder content of at least 5 weight percent (based on the total weight of the zeolite adsorbent particles) and when poured to form a bed, a defined effective zeolite crystal mass loading per volume of bed.

In one exemplary embodiment, the zeolite adsorbent particles of the present invention consists essentially of hydrophillic silica bound zeolite adsorbent particles having a mean diameter of greater than about 800 microns, a binder content of at least 5 weight percent (based on the total weight of the zeolite adsorbent particles) and when poured to form a bed, a defined effective zeolite crystal volume loading per volume of bed.

In one embodiment, the present invention provides a method of making silica bound zeolite adsorbent particles in accordance with the invention. In one exemplary method, the method of making comprises forming porous zeolite adsorbent particles bound with a silica binder, wherein the adsorbent particle have a mean diameter of greater than about 800 microns, a binder content of at least 5 weight percent (based on the total weight of the zeolite adsorbent particles) and when poured to form a bed an effective zeolite crystal mass loading per volume of bed.

In another exemplary embodiment, the method of making the zeolite adsorbent powder of the invention comprises mixing zeolite particles (e.g. a zeolite having a mean diameter in the range of about 1 to about 30 microns) and a silica binder and water followed by agglomeration and compaction of the zeolite/binder mixture in a mixer having a sufficient intensity and energy to form dense spherical particles. The particles are screened, dried and calcined to form the final zeolite adsorbent particles having a mean diameter of greater than about 800 microns, a binder content of at least 5 weight percent (based on the total weight of the adsorbent particles) and when poured to form a bed, an effective zeolite crystal mass loading per volume of bed.

In another embodiment, the method of making the zeolite adsorbent particles of the invention comprises mixing zeolite particles (e.g. a zeolite having a mean diameter in the range of about 1 to about 30 microns) and a silica binder and water followed by agglomeration and compaction of the zeolite/binder mixture in a mixer having a sufficient intensity and energy to form dense spherical particles. The particles are screened, dried and calcined to form the final zeolite adsorbent particles having a mean diameter of greater than about 800 microns, a binder content of at least 5 weight percent (based on the total weight of the adsorbent particles) and when poured to form a bed, an effective zeolite crystal mass volume per volume of bed.

In another exemplary embodiment, the present invention comprises silica bound zeolite adsorbent particles in accordance with the invention having a gas absorbed thereon. In one embodiment of the invention, the gas absorbed or loaded in the zeolite adsorbent particles of the invention is $CO_2$. In one embodiment of the invention, the gas absorbed or loaded in the zeolite adsorbent particles of the invention is Xe and or Sevoflurane.

In yet another exemplary embodiment, the present invention provide methods of using any of the gas loaded zeolite adsorbent particles of the invention in instant beverage carbonation processes, devices and systems. In one exemplary embodiment, the method comprises contacting $CO_2$ loaded zeolite adsorbent particles with a liquid displacement fluid to release $CO_2$ for dissolving into the liquid to eventually form a carbonated beverage. In one embodiment, the displacement fluid is water and/or other aqueous liquids suitable to form a carbonated beverage. In another embodiment, the gas loaded adsorbents of the invention is contained in a container. In yet another embodiment, the container is a cup, cartridge or bag.

In another embodiment of the invention, the method comprises placing the $CO_2$ loaded zeolite adsorbent particles contained within a container in an operating position within an instant beverage carbonation device or system; and processing a displacement fluid through the container to release $CO_2$ from the adsorbent particles for dissolving into the liquid to form a beverage.

In yet another exemplary embodiment, the present invention provide methods of using any of a medical gas loaded zeolite adsorbent particles of the invention in a method, process, or system for the delivery of medical gases, e.g. anesthesia gas, in single dose units. In one exemplary embodiment, the method comprises contacting an inhalation gas (e.g. Xe, Sevoflurane, etc . . . ) loaded zeolite adsorbent particles with a liquid displacement fluid to release the desired gas for inhalation for a desired medical purposes, e.g. anesthesia. In one embodiment, the displacement fluid is water. In another embodiment, the gas loaded adsorbents of the invention is contained in a container. In yet another embodiment, the container is a cup, cartridge or bag.

In another embodiment of the invention, the method comprises placing the medical gas loaded zeolite adsorbent particles contained within a container in an operating position within a portable medical device or system; and processing a displacement fluid through the container to release the desired medical gas for inhalation by a patient.

These and other features and advantages of the present invention will become apparent after a review of the following detailed description of the disclosed embodiments and the appended claims.

BRIEF DESCRIPTION OF THE FIGURES

FIG. 1 is a graphic representation of the $CO_2$ volumetric capacity of invention adsorbent as prepared in Examples 1-4 versus clay bound zeolite adsorbents.

DETAILED DESCRIPTION OF THE INVENTION

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

It must be noted that as used herein and in the appended claims, the singular forms "a", "and", and "the" include plural referents unless the context clearly dictates otherwise. Thus, for example, reference to "a zeolite" includes a plurality of such zeolite and reference to "zeolite" includes reference to one or more zeolite and equivalents thereof known to those skilled in the art, and so forth.

"About" modifying, for example, the quantity of an ingredient in a composition, concentrations, volumes, process temperatures, process times, recoveries or yields, flow rates, and like values, and ranges thereof, employed in describing the embodiments of the disclosure, refers to variation in the numerical quantity that may occur, for example, through typical measuring and handling procedures; through inadvertent error in these procedures; through differences in the ingredients used to carry out the methods; and like proximate considerations. The term "about" also encompasses amounts that differ due to aging of a formulation with a particular initial concentration or mixture, and amounts that differ due to mixing or processing a formulation with a particular initial concentration or mixture. Whether modified by the term "about" the claims appended hereto include equivalents to these quantities.

As used herein the term "adsorbents", or any form thereof, is used herein to indicate materials than can physically adsorb gases.

As used herein, the term "beverage" is used to indicate a liquid designed to be ingested by mammals with limited deleterious health effects.

As used herein, the term "bulk density" is defined as the grams of material per cc and is the density of a bed of activated adsorbent particles. In this application bulk density typically refers to a loose or poured bulk density in which the activated particles are poured into a cylinder of known volume without additional compaction or settling of any sort. The apparent density is different depending on the conditions of measurement. The measurement used in this invention is a loose bulk density which is poured into a vessel of fixed volume from a height of no greater than about 8 inches above the floor or bottom of the vessel with no significant agitation to stimulate compaction, unless otherwise specified.

As used herein, the term "carbonation" or "carbonated" is herein defined to generically refer to beverages that have a dissolved gas, and thus refers to a sparkling beverage whether the dissolved gas is carbon dioxide, nitrogen, oxygen, air or other gas. Thus, the herein mention of CO2 is not limited to forming beverages that have a dissolved carbon dioxide content, but rather may include any dissolved gas.

As used herein, the term "effective zeolite crystal mass loading within a bed" is a calculated value determined by dividing the volumetric adsorption capacity by the adsorption-capacity-by-mass determined for the pure (unbound) zeolite at the same temperature and adsorbate pressure used in determining the adsorption-capacity-by-mass for the bound particles.

As used herein, the term "effective zeolite crystal volume capacity within bed" is a calculated value determined by dividing the effective zeolite mass loading within bed by the crystal (skeletal) density of the activated zeolite crystals. The zeolite crystal densities can be determined by mercury porosimetry or calculated knowing the anhydrous zeolite composition and unit cell dimensions. The crystal density for the NaX zeolite used in the examples given in this application is approximately 1.44 g/cc.

As used herein the term "displacement fluid" as it relates to an instant beverage carbonation process, device or system is used herein to indicate a fluid that is more strongly adsorbed on the adsorbent relative to the gas that is desired to be released.

As used herein the term "instant" is used herein to indicate that the gas reversibly adsorbed on the adsorbent is released for incorporation into the target fluid at the time of use of the end beverage.

As used herein the term "intra-particle pore volume is used herein to indicated the total pore volume within an zeolite adsorbent aggregate particle excluding the volume of pores within the zeolite crystals themselves, that is excluding the volume of pore having a diameter of less than 40 Å, as measured by mercury pre volume.

As used herein the term "mass capacity" or "adsorption capacity by mass" is defined as the grams of gas per 100 g of adsorbent and indicates the mass of adsorbate gas adsorbed in a bed of silica bound zeolite particles at equilibrium expressed as mass of adsorbed gas per mass of adsorbent particles (determined before the adsorption process. The volumetric capacity is the product of the mass capacity and bulk density.

As used herein the term "mean diameter" is used to indicate the average diameter of a particle size distribution, average over the number of particles.

As used herein the terms "particle" or "particles" are used herein to indicative respectively a particle or particle that are aggregate bead(s) or pellet(s) having a generally spherical or spheroidal shape or form.

As used herein the term "portable" is used herein to indicate that the gas reversibly adsorbed on the adsorbent is released for inhalation at the time of use of the medical gas, and the gas container contains a single dose of medical gas.

As used herein the term "volumetric gas capacity" or "volumetric capacity for the adsorption of gas" is defined as the grams of gas per 100 cc of adsorbent packed in a loose bed. The volumetric capacity is the product of the mass capacity and the bulk density.

As used herein, "zeolite" is defined as a group of, crystalline metal aluminosilicates which exhibit a network of $SiO_4$ and $AlO_4$ tetrahedral in which aluminum and silicon atoms are crosslinked in a three-dimensional framework by sharing oxygen atoms. In the framework, the ratio of oxygen atoms to the total of aluminum and silicon atoms is approximately equal to 2. The framework exhibits a negative electrovalence that typically is balanced by the inclusion of cations within the crystal such as metals, alkali metals, alkaline earth metals, or hydrogen.

Zeolites useful to prepare the adsorbent particles of the present invention may be a natural or synthetic aluminosilicate minerals that typically contain alkali and alkaline metals. The zeolites are characterized by a framework structure that encloses interconnected cavities occupied by ion-exchangeable metal cations such as potassium and water molecules permitting reversible dehydration. The actual formula of the zeolite may vary without changing the crystalline structure. Two basic types of crystalline aluminosilicate molecular sieves most readily available on a commercial scale have been given the art-recognized designations of "Zeolite X" and "Zeolite A". Other molecular sieves which have been synthesized include Y-zeolite, omega zeolite, beta zeolite, ZSM-4, ZSM-5, ZSM-10, ZSM-12, ZSM-20, REY, USY, RE-USY, LZ-210, LZ-210-A, LZ-21M, LZ-210-T, SSZ-24, ZZA-26, SSZ-31, SSZ-35, SSZ-37, SSZ-41, SSZ-42, mordenite, faujasite, or combinations thereof. These and other types of zeolites useful in the this invention are described more fully in the following publications incorporated herein by reference: Hersh, Molecular Sieves, Reinhold Publishing Corporation, 1961; Thomas and Mays, "Separations with Molecular Sieves" found at pages 45-97 of Physical Methods in Chemical Analysis, Volume IV, edited by Walter G. Berl, Academic Press, 1961; Breck, "Crystalline Molecular Sieves", found at page 678 of the Journal of Chemical Education, Volume 41, December, 1964; and "Linde Molecular Sieves," a technical publication of the Union Carbide Corporation.

In one embodiment of the invention, the zeolite is one having an effective pore diameter of from about 4 Angstroms (Å) to about 10 Å, alternatively from about 7 Å to about 9 Å. Crystalline zeolites suitable for use in this invention include without limitation, X-zeolite, Y-zeolite, omega zeolite, beta zeolite, ZSM-4, ZSM-5, ZSM-10, ZSM-12, ZSM-20, REY, USY, RE-USY, LZ-210, LZ-210-A, LZ-210-M, LZ-210-T, SSZ-24, ZZA-26, SSZ-31, SSZ-33, SSZ-35, SSZ-37, SSZ-41, SSZ-42, SSZ-44, mordenite, faujasite, or combinations thereof. In an embodiment of the invention, the zeolite comprises zeolite X, zeolite A or a combination thereof. In another embodiment of the invention the zeolite is zeolite X, in particularly, zeolite 13X.

In one embodiment, zeolites useful to prepare the zeolite particles of the invention, have a mole ratio of silica to alumina ($SiO_2/Al_2O_3$) of less than 6. In another embodiment, the zeolite useful to prepare adsorbent of the invention is zeolite having a $SiO_2/Al_2O_3$ of about 2 to about 5.0. In yet another embodiment of the invention, the zeolite is a zeolite X having a mole ratio of $SiO_2/Al_2O_3$ of about 2 to about 3.

Generally, the zeolites used to prepare the invention adsorbents are in the form of powders having a mean particle diameter ranging from about 1.0 to about 30 microns. In one embodiment of the invention the starting zeolites have a mean particle diameter ranging from about 1.5 to about 20 microns. In another embodiment of the invention the starting zeolites have a mean particle diameter ranging from about 2 to about 10 microns.

Silica containing binders used to prepare the adsorbents of the invention include a binder selected from the group consisting of colloidal silica, silicic acid, an alkali metal silicate or a combination thereof. In one embodiment, the binder is a hydrophilic binder. In another embodiment of the invention, the binder is a hydrophilic colloidal silica. In one embodiment the silica is colloidal silica having an mean particle diameter ranging from about 5 to about 100 nm. In another embodiment, the colloidal silica binder has a mean particle diameter from about 7 to about 85 nm. Suitable colloidal silica useful in the present invention include Ludox®SM, Ludox®HS-40, Ludox®™-50 and Ludox®PW-50E which may be obtained from W.R. Grace & Co.-Conn in Columbia, Md. In one embodiment, the binder comprises silicic acid or an alkali metal silica. Suitable silicic acid is prepared by treatment of an alkali metal silicate with cation exchange resin such as described and disclosed in U.S. Pat. No. 3,649,556. Alkali metal silicates useful in the present invention include alkali silicates, such as Crystal® L lithium silicates, Kasil® Potassium Silicates or Metso® Na silicates from PQ corporation.

Typically, the content of the silica containing binder in the zeolite adsorbent particles of the invention is not less than 5 weight percent, based on the total weight of the adsorbent particles. In one embodiment of the invention, the content of the binder in the adsorbent particles ranges from about 5 weight percent to about 20 weight percent, based on the total weight of the adsorbent particles. In another embodiment of the invention, the content of the binder in the adsorbent particles ranges from about 10 weight percent to about 15 weight percent, based on the total weight of the adsorbent particles.

Adsorbent particles of the invention may vary in shape and/or form depending upon the intended use of the adsorbents. In one embodiment of the invention, the adsorbents are spherical or spheroidal in shape and are generally in the form of beads. In another embodiment, however, the adsorbent particles have a cylindrical shape and may be in the form of pellets or extrudates.

Generally, the zeolite adsorbent particles of the invention have a mean diameter of greater than about 800 microns. In another embodiment of the invention the zeolite adsorbent particles of the invention have a mean diameter ranging from about 850 to about 3000 microns. In some embodiments of the invention, the zeolite adsorbent particles of the invention, have a mean diameter ranging from about 900 to about 2000 microns. The specified mean diameter as described herein above and throughout this disclosure are the average particles sizes and reference herein refers to a group of adsorbent particles distributed over a range of particles size, i.e. particle size distribution.

The properties of the zeolite adsorbent particles (i.e. pore volume, crush strength, attrition resistance, density, volumetric capacity etc . . . ) can be highly dependent upon the method of preparing the particles. Generally, the particles are prepared by homogeneously mixing zeolite powders (e.g. a zeolite having a mean diameter ranging from about 1 to about 10 microns), a silica containing binder material comprising colloidal silica, silicic acid, alkali metal silicate and combinations thereof, and water. In one embodiment of the invention, the zeolite powder and aqueous binder slurry are mixed with water to a point below excipient wetness of the zeolite powder.

In one embodiment, the silica containing binder material is present as an aqueous slurry which comprises from about 15 to about 50 weight percent silica, based on the total weight of the slurry. In some embodiments of the invention, the aqueous slurry comprises from about 30 to about 40 of silica, based on the total weight of the slurry. In yet another embodiment of the invention, the pH of the aqueous binder slurry is adjusted to reduce the basicity of the slurry prior to mixing with the zeolite powder. In one embodiment of the invention, the binder solution pH is adjusted to a pH of 8 or less. In another embodiment of the invention, the pH of the binder solution is adjusted to about 3 to about 8. In yet another embodiment, the pH of the slurry is adjusted to about 7.

In an exemplary embodiment of the invention, the zeolite/binder mixture is agglomerated and compacted to form dense spherical particles. In one embodiment, the zeolite/binder mixture is agglomerated and compacted in a mixer having an intensity and energy sufficient to form dense spherical particles, pellets or beads. Mixing times for the agglomeration compaction phase will vary, however, is typically from about 5 to about 60 minutes. Suitable mixers capable of forming the adsorbent particles of the invention include Eirich® mixer, Nauta® mixer, High Energy mixer, and Rotomix® mixer. In one embodiment, the mixer is an Eirich mixer. In another embodiment of the invention, mixing, agglomeration and compaction are performed simultaneously.

In an alternative embodiment of the invention, the zeolite/binder mixture is formed into a cylindrical shape using conventional extrusion techniques.

Following forming, aggregrate adsorbent particles of the invention are screened as necessary to obtain the desired range of particle sizes and is thereafter dried to remove excess moisture. In one embodiment the particles are dried at a temperature ranging from about 250° F. to about 400° F. The formed particles are thereafter calcined at high temperatures to set the binder material and activate the zeolite for gas adsorption. In one embodiment the formed particles are calcined at a temperature ranging from about 600° F. to about 1200° F. and from a time ranging from about 10 minute to about 2 hours. In one embodiment of the invention, the calcination temperature ranges from about 900° F. to about 1100° F. for about 10 minutes to about 1 hour. In both the drying step and the calcination steps, the material is dried or calcined under conditions to prevent steaming of the material that could damage the zeolite and impact the gas adsorption capacity of the beads. Conditions of low bead bed depths, air flow through the bed and sweep across the material are preferred.

The zeolite adsorbent particles of the invention possess an average crush strength equilibrated with an excess of water (i.e. wet) of at least 2 lbf, as measured by the single bead crush strength method. In one embodiment of the invention, the formed zeolite adsorbent aggregates have an average crush strength (wet) of about 2.0 lbf to about 8.0 lbf. The final zeolite adsorbent particles of the invention possess an Attrition Index of less than 0.15 wt % as measured by the Breakage/Attrition Simulated Use Test (SUT). In one embodiment of the invention, the zeolite adsorbent particles possess a SUT Attrition Index ranging from about 0 to about 0.15 wt %. The high crush strength and attrition resistance affords the zeolite adsorbents of the invention greater resistance to degradation during use and shipping than prior used clay bound zeolite aggregates.

The dense adsorbent particles of the invention provide less pore volume, greater density and greater adsorbent capacity per unit bed volume than traditionally clay bound zeolite adsorbents. Adsorbent particles of the invention have a bulk density of at least 0.5 g/cc. In one embodiment the bulk density ranging from about 0.5 g/cc to about 0.7 g/cc.

On the other hand, the intra-particle pore volume of the invention adsorbents is relatively low as compared to a clay bound zeolite adsorbent. In one embodiment, the adsorbent particles of the invention possess an intra particle pore volume of no greater than 0.28 cc/gas determined by mercury porosimetry. In some embodiments of the invention, the invention adsorbents possess an intra particle pore volume ranging from about 0.18 to about 0.26 cc/g. In other embodiments of the invention, the invention adsorbents possess an intra particle pore volume ranging from about 0.18 to about 0.26 cc/g. Advantageously, when poured into a loosely packed bed, the adsorbents of the invention possess a zeolite crystal density within the bed to provide a high mass loadings of zeolite crystals per unit volume of the bed and, correspondingly, a high volumetric loading of zeolite crystals per unit volume of bed. In one embodiment of the invention, the zeolite crystal density within the loose bed is sufficient to provide an effective zeolite crystal mass loading (gm zeolite/100 cc of bed) of at least 52 g/100 cc of bed. In another embodiment, the zeolite crystal density within the loose bed is sufficient to provide an effective zeolite crystal mass loading (gm zeolite/100 cc of bed) ranging from about 52 to about 65 g/100 cc of bed. In one embodiment, the effective zeolite crystal volume loading (cc zeolite/100 cc of bed) is at least 36 g/100 cc. In another embodiment, the effective zeolite crystal volume loading (cc zeolite/100 cc of bed) ranges from about 36 to about 46 cc/100 cc. Consequently, beds of the inventive adsorbent have high volumetric adsorption capacity compared to beds made with typical clay-bound zeolitic adsorbents crystal. Further, given its relatively low intra-particle pore volume, the adsorbents of the invention unexpectedly exhibits rapid desorption rates when an adsorbed gas is desorbed by addition of a more strongly adsorbed displacing fluid. Typical the desorption rate of absorbents of the invention is at rate such that at least 75% of an absorbed gas can be desorbed from the absorbent particles within 30 seconds when the adsorbent particles containing an absorbed gas are wetted with a volume of water in excess of the volume of the gas containing absorbents.

Adsorbents in accordance with the present invention addresses some of the difficulties and problems heretofore associated with adsorbent material typically used as a gas source in such applications. The invention adsorbents enable a more efficient, productive and effective means of enhancing gas concentrations in a confined space due to one or more of the following advantages over the use of conventional clay bound zeolite materials: greater particle density; higher volumetric gas capacity; low dust creation; high resistance to particle breakage and attrition; elimination of quartz crystals; minimization of heavy metals, e.g. very low heavy metals content; high particle integrity; high zeolite content; and low binder content.

A balance of high adsorption capacity, good desorption rate and high particle strength enable the adsorbents of the invention to be useful as a gas source in various volumetrically constrained environments. In preparation for use as a gas source, the adsorbents may be "loaded" with an amount of gas sufficient to provide a desired amount of gas for the intended application. Suitable gases for loading on the adsorbents in accordance with the invention include, but are not limited to $H_2O$, $CO_2$, $NH_3$, $SO_2$, $SO_x$, $NO_x$, $CH_4$, C2-C8 hydrocarbons, $N_2$, $O_2$, $H_2S$, He, Kr, Ar, Ne, Xe, desflurane, diethyl ether methoxypropane, vinyl ether, halogenated ethers, enflurane, isoflurane, methoxyflurane, sevoflurane, chloroform, halothane, trichloroethylene or combinations thereof. In one embodiment of the invention, the gas loaded onto the silica bound absorbents of the invention include desflurane, enflurane, isoflurane, $N_2O$ or combinations thereof. In another embodiment the gas is $CO_2$. In yet another embodiment the gas is desflurane.

The desired gas may be loaded on the adsorbents using any conventional means. In one embodiment, gas is loaded by contacting the activated (i.e., at least partially dehydrated) adsorbent with a gas, i.e. gaseous $CO_2$, under anhydrous conditions to bring about absorption of the gas. Typically, the adsorbent of the invention can be dehydrated to about 0.5% by weight water. In one embodiment the adsorbent particles are charged with the desired gas in a packed bed column to which the gas is passed in ambient temperature and at a slight positive pressure (up to 0.5 psig). However, the extent to which the invention adsorbent is loaded with a desired gas will vary depending upon the requirements of the intended process, device or system of use.

Typically, when used, gas loaded adsorbents of the invention will be contained in a container. In one embodiment, the container is a cup, cartridge or bag. In another embodiment of the invention the gas loaded adsorbent is contained in a impermeable container. The manner of use of gas loaded adsorbent within a process, device, or system will vary depending on the particulars of the same. It is within the scope of this invention to use the adsorbent in any device, process, or system typically using clay bound zeolite material as a gas source.

In one embodiment of the invention, the adsorbents of the invention are loaded with $CO_2$ and the loaded adsorbents are used as a gas source in an instant beverage carbonation process and device. In this embodiment, the adsorbents should be loaded to the extent of at least about 18% by weight (i.e., weight of $CO_2$ adsorbed/weight of adsorbent.times.100%). The high bulk density of the invention adsorbent provides an increased capacity for $CO_2$ adsorption as the denser particles provide more zeolite by weight per unit volume. $CO_2$ loaded adsorbent having a volumetric capacity of $CO_2$ of at least 13.0 g $CO_2$/100 cc of adsorbent are obtainable using the process of the present invention. In one embodiment of the invention, the adsorbent particles of the invention have a volumetric capacity of $CO_2$ of at least 14.0 g $CO_2$/100 cc of adsorbent. In another embodiment of the invention, the adsorbent particles of the invention have a volumetric capacity of $CO_2$ ranging from about 13.0 to about 17.0 g $CO_2$/100 cc of adsorbent. In yet another embodiment of the invention, the adsorbent particles of the invention have a volumetric capacity of $CO_2$ ranging from about 13.5 to about 16.0 g $CO_2$/100 cc of adsorbent.

The $CO_2$ loaded adsorbents may be used in any instant beverage carbonation processes, devices and systems in which clay bound zeolite adsorbents are typically used; such as for example, those disclosed and described in U.S. Patents and/or Patent Publications U.S. Pat. Nos. 4,025,655; 4,100,255; US 2011/0226343 A1; and US2013/0129870 A1, inter alia., said references herein incorporated by reference. In such cases, carbon dioxide loaded adsorbents are contacted with aqueous potable liquid to facilitate the carbonation process. In one embodiment of the invention, the invention adsorbents are used by placing the gas loaded particles contained within a container in an operating position within the instant beverage carbonation device or system; and processing a replacement liquid through the container to release $CO_2$ from the adsorbent particles for dissolving into the liquid to form a beverage. Carbon dioxide is released from the adsorbent particles by the preferential adsorption of water from a replacement fluid. In one embodiment, the replacement fluid is water and/or other aqueous liquid suitable to form a carbonated beverage. A carbonated beverage results when this released carbon dioxide is dissolved in another aqueous liquid. The degree of carbonation is typically described as "volumes of dissolved $CO_2$" or "volumes of carbonation" defined as the volume of gas (reduced to standard conditions, i.e., 760 mmHg and 32° F.) which at the temperature and pressure of carbonation is dissolved in a given volume of beverage.

In another embodiment of the invention, the adsorbents are loaded with a medical gas and the loaded adsorbents are used as a gas source in a portable medical gas dispensing unit, such as described in US Patent Publication No. US2009/0071481, which reference is herein incorporated by reference. In one embodiment of the invention, the absorbents of the invention loaded with a desired medical gas is used by placing the gas loaded particles contained within a container in an operating position within the portable medical gas dispensing unit, device or system; and processing a replacement liquid through the container to release the desired gas, e.g. e.g. anesthesia gas, from the adsorbent particles for direct inhalation by a patient.

To further illustrate the present invention and the advantages thereof, the following specific examples are given. The examples are given as specific illustrations of the claimed invention. It should be understood, however, that the invention is not limited to the specific details set forth in the examples. It is to be clearly understood that resort may be had to various other embodiments, modifications, and equivalents thereof which, after reading the description herein, may suggest themselves to those skilled in the art without departing from the spirit of the present invention and/or the scope of the appended claims.

All parts and percentages in the examples as well as the remainder of the specification which refers to solid compositions or concentrations are by weight unless otherwise specified. However, all parts and percentages in the examples as well as the remainder of the specification referring to gas compositions are molar or by volume unless otherwise specified.

Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited.

EXAMPLES

The following examples describe a process in accordance with the present invention for the preparation and evaluation of silica bound adsorptions in accordance with the invention.

The pore volume of the invention adsorbents were determined by Hg pore volumes using the Autopore iv 9500 apparatus using the intrusion data. A contact angle of 140° was assumed. The pore volume was calculated based on the intrusion volume between approximately 220 and 53000 psia which corresponds to the range of pore sizes between 40 and 100000 Angstroms. This range was chosen in order to determine the total volume of intra-particle pores excepting those with the zeolite crystals.

Breakage and Attrition were measured using a Simulated Use Test. This test was designed to measure the dust and fine particles generated in a simulated use test where activated adsorbent is equilibrated with $CO_2$ gas at one atmosphere then rapidly exposed to a significant volume of water thus subjecting the product to the combined effects of rapid wetting, rapid heating (due to heat of adsorption effects) and rapid buildup of internal pressure due to $CO_2$ desorption.

Specifically, a sample of dry adsorbent is activated for two hours in an oven at 450° C. (bed depth less than 0.25 inches) and cooled to ambient temperature so as to avoid moisture pick-up. The sample is then equilibrated with 1 atmosphere of flowing $CO_2$ at atmospheric pressure and ambient temperature until equilibrium is achieved (typically about two hours when $CO_2$ gas is flowed through a 50 gram bed at 0.4 liters/minutes). Fifty grams of the $CO_2$ equilibrated sample is quickly placed into a dry 600 ml beaker. Immediately, fifty grams of ambient temperature DI water is poured into the beaker onto the adsorbent resulting in vigorous frothing as the $CO_2$ is rapidly desorbed. After two minutes the contents of the beaker are poured into a glass tray and the beaker is rinsed thoroughly with this liquid also being poured into the same tray. The tray is placed into a 110° C. drying oven for at least 12 hours to ensure complete drying of the solid. After drying, the solid residue (which typically includes powder and both broken and unbroken beads is then screened onto a 30 mesh screen (or slightly larger or smaller mesh chosen so that whole beds will not pass through but broken beads and powder will). The powder and broken beads that pass through the screen into the pan are then weighed. This complete procedure is done twice with the results averaged and the result is reported as a weight % of the initial $CO_2$ loaded sample (~50 grams).

The $CO_2$ adsorption capacity was determined on the invention adsorbents of the examples using the following method: The $CO_2$ adsorption capacity was carried out in a controlled environment where the ambient pressure is between 750 and 770 Torr and the ambient temperature is between 21 and 23° C. Approximately 20 g of thermally activated adsorbent beads (450° C. for 2 hours with bed depth less than 1 cm. and cooled in a sealed container to prevent moisture pick-up) are placed in a pre-weighed Schwartz drying tube (Fischer part #09-230B) and reweighed after filling. The drying tube is attached to a $CO_2$ source with flowing $CO_2$ at a rate of approximately 200 cc/min, ensuring the inlet pressure to the tube does not exceed a pressure of 1" of $H_2O$ (gauge). The temperature of the $CO_2$ at the inlet to the adsorption bed should be within 1° C. of ambient temperature. After 2.5 hrs the drying tube is removed from the CO2 and weighed. The drying tube is reconnected to the flowing CO2 for additional 30 min increments and weighed until no further increases are observed. Calculated wt % CO2 adsorbed is calculated as follows: WT %=((final weight of tube and adsorbent initial weight of tube and adsorbent)/(initial weight of tube and adsorbent−empty tube weight))×100.

The desorption rate of gas loaded adsorbents of the invention was determined using the following CO2 Desorption Rate Test. The desorption rate test is carried out in a multi-neck 250 ml round bottom flask. A standard taper adapter containing a septum is placed in the middle neck and standard taper adapters connected to ⅛ inch diameter tubing in the other necks. Before making a desorption rate measurement, the flask is continuously purged with flowing dry CO2 gas (>160 cc/min) to displace air and moisture for a minimum of twenty minutes. A 2+/−0.04 g sample of activated adsorbent is then weighed (recording the exact mass) and then quickly placed into the flask so as to minimize water pick-up by the sample. (Thermal activation is carried out at for 2 hrs at 450° C. with a bed depth of 1 cm or less and the sample is cooled in a sealed can or jar to prevent moisture pick-up during cooling.) CO2 flow through the flask is then continued for at least 3 hours to ensure an equilibrium loading of CO2 on the adsorbent (at approximately 760 torr and 22° C.). At this point the CO2 flow is stopped and the flask ports sealed to prevent CO2 leakage from the flask. A water-filled, inverted graduated cylinder is used to capture and measure desorbed gas during the test. A ⅛ inch plastic line is connected to one side-port of the flask with the other end placed into the inverted graduated cylinder (partially submerged in a water reservoir to maintain complete water-filling of the graduated cylinder prior to the desorption test). A 50 cc syringe is filed with 8±0.5 gms of water and gross weight recorded. The syringe needle is pushed through the septum into the flask and the water is quickly injected into the flask while simultaneously starting a timer. Desorbed gas volumes collected in the graduated cylinder are recorded at 5, 10, 15, 20, 25, 30, 40, 50, 60, 90, 120 seconds, and if necessary at 30 second intervals thereafter until no more CO2 is being desorbed. The 50 cc syringe is then reweighed to determine the mass of water injected into the flask. The approximate volume of the injected water is subtracted from the recorded gas volumes to give adjusted desorbed gas volumes. The 30 second desorption rate is calculated by dividing the adjusted volume of gas (CO2) desorbed at 30 seconds by the adjusted volume of gas desorbed at equilibrium with the value expressed as a percentage.

Example 1

Un-activated Zeolite 13X powder (2300 g) was placed in an Eirich Mixer (Type R02). While mixing on high rotating tool speed and low rotating pan speed, 1100 g of pH 7 adjusted colloidal silica binder solution (795.5 g Ludox® HS-40+~46 g 9% H2SO4+balance of H2O) was added slowly followed by additional mixing for 8.5 min. The mixer was stopped, walls of the pan scraped followed by mixing (high rotary tool, low pan speed) for 3.0 min. While running the mixer on low rotor speed and low pan speed water was added in increments of 25 ml, 10 ml, 10 ml, 10 ml and 5 ml with continued 5.0 min mixing periods after each addition. The beads formed were on the order 1.72 mm. The beads were dried at 250 F overnight followed by calcination at 1050 F for 2.5 hrs (TV (1750 F, 1 hr)=1.23% CO2 adsorption=21.8 wt %, Bulk density=0.675 g/cc).

Example 2

Un-activated Zeolite 13X powder (2300 g) was placed in an Eirich Mixer (Type R02). While mixing on high rotating tool speed and low rotating pan speed, 1100 g of pH 7 adjusted colloidal silica binder solution (795.5 g Ludox® HS-40+~46 g 9% H2SO4+balance of H2O) was added slowly followed by additional mixing for 8.5 min. The mixer was stopped, walls of the pan scraped followed by mixing (high rotary tool, low pan speed) for 3.0 min. While running the mixer on low rotor speed and low pan speed 10 ml of water was added followed by 10 min of mixing. Further additions of water in increments of 5 ml, with continued 5.0 min mixing periods after each addition was repeated 8 times followed by a final 5 ml of water addition and a mix time of 10 min. The beads formed were on the order 1.60 mm. The beads were dried at 250 F overnight followed by calcination at 1050 F for 2.5 hrs (TV (1750 F, 1 hr)=1.21%, CO2 adsorption=21.3 wt %, Bulk density=0.704 g/cc).

Example 3

Un-activated Zeolite 13X powder (2300 g) was placed in an Eirich Mixer (Type R02). While mixing on high rotating tool speed and low rotating pan speed, 1100 g of pH 7 adjusted colloidal silica binder solution (795.5 g Ludox® HS-40+~46 g 9% H2SO4+balance of H2O) was added slowly followed by additional mixing for 8.5 min. The mixer was stopped, walls of the pan scraped followed by mixing (high rotary tool, low pan speed) for 3.0 min. While running the mixer on low rotor speed and low pan speed 15.6 ml of water was added followed by 10 min of mixing. Further additions of water in increments of 4.8 ml, 4.9 ml, 4.8 ml, 4.7 ml, 5.5 ml, 6.1 ml, and 3.6 ml with continued 5.0 min mixing periods after each addition. The beads formed were on the order 1.60 mm. The beads were dried at 250° F. overnight followed by calcination at 1050 F for 2.5 hrs (TV (1750 F, 1 hr)=1.15%, CO2 adsorption=21.8 wt. %, Bulk density=0.696 g/cc).

Example 4

Un-activated Zeolite 13X powder (2300 g) was placed in an Eirich Mixer (Type R02). While mixing on high rotating tool speed and low rotating pan speed, 1100 g of pH 7 adjusted colloidal silica binder solution (795.5 g Ludox® HS-40+~46 g 9% H2SO4+balance of H2O) was added slowly followed by additional mixing for 8.5 min. The mixer was stopped, walls of the pan scraped followed by mixing (high rotary tool, low pan speed) for 3.0 min. While running the mixer on low rotor speed and low pan speed 22.7 ml of water was added followed by 10 min of mixing, then 11.3 ml was added followed by 5 min of mixing and finally 8.5 ml water was added followed by 10 min of mixing. The beads formed were on the order 1.76 mm. The beads were dried at 250 F overnight followed by calcination at 1050 F for 2.5 hrs (TV (1750 F, 1 hr)=1.19%, CO2 adsorption=21.5%, Bulk density=0.678 g/cc).

Evaluations of the adsorbent products described in Examples 1-4 are given in Table 1 along with corresponding evaluations of two commercial clay bound NaX beads for comparison. Results demonstrate the greater bulk densities and mass CO2 adsorption capacities of the inventive products of examples 1-4 compared to the clay-bound adsorbent products. This combination of properties results in a significantly greater volumetric CO2 capacity for the inventive products. The inventive products also show lower Hg pore volume (lower intra-particle pore volume) and lower Breakage/Attrition Index compared to the clay-bound NaX samples. FIG. 1 shows the greater volumetric CO2 capacity of inventive products described in examples 1-4 compared to the clay-bound NaX products. The FIGURE shows the relative contributions of density and mass capacity (g Adsorbate/100 g adsorbent) to the improved volumetric adsorption capacities. Dashed lines in the FIGURE represent lines of constant volumetric adsorption capacity.

whenever a numerical range with a lower limit, $R_L$, and an upper limit $R_U$, is disclosed, any number R falling within the range is specifically disclosed. In particular, the following numbers R within the range are specifically disclosed: $R=R_L+k(R_U-R_L)$, where k is a variable ranging from 1% to 100% with a 1% increment, e.g., k is 1%, 2%, 3%, 4%, 5% . . . 50%, 51%, 52% . . . 95%, 96%, 97%, 98%, 99%, or 100%. Moreover, any numerical range represented by any two values of R, as calculated above is also specifically disclosed. Any modifications of the invention, in addition to those shown and described herein, will become apparent to those skilled in the art from the foregoing description and Evaluation of Inventive Adsorbents (Examples 1-4) Versus Clay BoundNaX Adsorbents

|  | Examples | | | | Clay Bound NaX Adsorbent Samples | |
|---|---|---|---|---|---|---|
|  | 1 | 2 | 3 | 4 | A[3] | B[4] |
| Composition | | | | | | |
| Adsorbent | NaX | | | | NaX | NaX |
| Binder Type | Colloidal Silica (Ludox HS-40) | | | | Clay | Clay |
| Binder (wt %) | 15 | | | | 18 | — |
| Physical Properties | | | | | | |
| Particle Size (mm) | 1.7 0.6 | 1.6 0.7 | 1.6 0.6 | 1.8 0.6 | 1.9 | 2.3 |
| Bulk Density. (g/cc) | 75 0.2 | 04 0.2 | 96 | 78 | 0.635 | 0.632 |
| Hg Pore Volume (cc/g) | 3 | 2 | — | — | 0.29 | 0.31 |
| Crush Str. (lbf) | | | | | | |
| Dry | 5.5 | 7.2 | 4.6 | 5.7 | 6.5 | 8.3 |
| Wet | 2.3 0.0 | 3.5 | 2.9 0.0 | 3.1 0.0 | 2.2 | 2.7 |
| Breakage/Attrition Index (SUT) | 8 | — | 7 | 7 | 0.14 | 0.27 |
| CO2 Adsorption Capacity | | | | | | |
| By Mass (gCO$_2$/100 g Ads) | 21.8 | 21.3 | 21.8 | 21.5 | 21.1 | 19.4 |
| Volumetric (gCO$_2$/100 cc Ads) | 14.7 | 15.0 | 15.2 | 14.6 | 13.4 | 12.3 |
| Zeolite crystal density within loose bed of adsorbent | | | | | | |
| Effective zeolite crystal mass loadings (gm zeol./100 cc of bed)[1] | 56.8 | 57.9 | 58.6 | 56.3 | 51.7 | 47.5 |
| Effective zeolite crystal volume loading (cc zeol./100 cc of bed)[2] | 38.9 | 39.7 | 40.1 | 38.5 | 35.4 | 32.5 |
| Desorption Kinetics | | | | | | |
| CO$_2$ Des. in 30 sec. (%) | 97.2 | 93.9 | 98.3 | 95.8 | 97.9 | 90.6 |

[1]Calculated based on NaX zeolite powder CO2 ads. capacity of 25.9%
[2]Calculated based on NaX powder skeletal density of 1.46 g/cc
[3]C-548 NaX adsorbent from W. R. Grace
[4]13X beads (8-12 m) from Shanghai Hengye Chemical Industry Co. LTD While the invention has been described with a limited number of embodiments, these specific embodiments are not intended to limit the scope of the invention as otherwise described and claimed herein. It may be evident to those of ordinary skill in the art upon review of the exemplary embodiments herein that further modifications, equivalents, and variations are possible. All parts and percentages in the examples, as well as in the remainder of the specification, are by weight unless otherwise specified. Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited. For example, accompanying drawings. Such modifications are intended to fall within the scope of the appended claims. All publications cited herein are incorporated by reference in their entirety.

We claim:

1. A plurality of adsorbent particles, wherein the particles comprise zeolite powders bound with a silica binder, wherein the zeolite has a silica to alumina ($SiO_2/Al_2O_3$) ratio of less than 6 and wherein the silica binder content in the particles is at least 5 wt %, based on the total weight of the particles; wherein the adsorbent particles have a mean diameter of greater than 800 microns and
   a) a zeolite crystal density within a loose bed sufficient to provide an effective zeolite crystal mass loading within the bed of at least 52 g/100 cc, and/or b) a zeolite crystal density within a loose bed sufficient to provide an effective zeolite crystal volume loading within the bed of at least 36 cc/100 cc, or c) a volumetric capacity for $CO_2$ of at least 13.4 g $CO_2$/100 cc of adsorbent.

2. The adsorbent particles of claim 1 wherein the particles have an intra-pore volume of no greater than 0.28 cc/g.

3. The adsorbent particles of claim 1 wherein at least 75% of an adsorbed gas can desorbed from the adsorbent particles containing a desired gas within 30 seconds when the adsorbent particles are wetted with a volume of water in excess of the volume of the gas containing adsorbent.

4. Adsorbent particles of claim 1 wherein the silica binder is selected from the group consisting of colloidal silica, silicic acid, alkali metal silicate and combinations thereof.

5. Adsorbent particles of any one of claim 1 wherein the particles have an average crush strength of at least about 2.0 lbf.

6. Adsorbent particles of claim 1 wherein the particles have a bulk density of at least about 0.5 g/cc.

7. Adsorbent particles of claim 1 wherein the particles have an Attrition Index of less than about 0.15, as measured by the SUT test.

8. Adsorbent particles of claim 1 wherein the particles are spherical in shape.

9. Adsorbent particles of claim 1 wherein the particles have a mean diameter ranging from about 850 to about 3000 microns.

10. Adsorbent particles of claim 1 wherein the particles have a pore volume, as determined by mercury porosimetry, of ranging from about 0.15 to about 0.28 cc/g.

11. Adsorbent particles of claim 1 wherein the zeolite comprises X-zeolite, Y-zeolite, A-zeolite, omega zeolite, beta zeolite, ZSM-4, ZSM-5, ZSM-10, ZSM-12, ZSM-20, REY, USY, RE-USY, LZ-210, LZ-210-A, LZ-210-M, LZ-210-T, SSZ-24, ZZA-26, SSZ-31, SSZ-33, SSZ-35, SSZ-37, SSZ-41, SSZ-42, SSZ-44, mordenite, faujasite, or combinations thereof.

12. Adsorbent particles of any one of claims 1 to 11 having a gas reversibly adsorbed therein, wherein the gas is $H_2O$, $CO_2$, $NH_3$, $SO_2$, $SO_x$, $NO_x$, $CH_4$, $C_2$-$C_8$ hydrocarbons, $N_2$, $O_2$, $H_2S$, He, Kr, Ar, Ne, Xe, desflurane, diethyl ether-.methoxypropane, vinyl ether, halogenated ethers, enflurane, isoflurane, methoxyflurane, sevoflurane, chloroform, halothane, trichloroethylene or combinations thereof.

13. Adsorbent particles of claim 12 wherein the adsorbent particles are contained in a container.

14. A plurality of adsorbent particles according to claim 1 wherein in c) the zeolite of the particles has a silica to alumina ($SiO_2/Al_2O_3$) ratio of less than 3 and wherein the adsorbent particles have a volumetric capacity volumetric capacity of at least 13.4 g $CO_2$/100 cc of adsorbent.

15. An instant beverage carbonation device or system comprising the adsorbent of claim 1.

16. A portable medical gas delivery device or system comprising the adsorbent of claim 1.

17. A method of manufacturing dense adsorbent particles having a high volumetric capacity, the process comprising:
mixing zeolite powder, a silica binder and water in an amount sufficient to form a homogeneous mixture;
forming the zeolite/silica mixture to provide dense adsorbent particles having a mean particle diameter of greater than 800 microns;
drying the particles; and
calcining the dried particles to provide silica bound zeolite particles having at least 5 wt %, based on the total weight of the particles, of a silica binder, a mean diameter of greater than 800 microns and a zeolite crystal density when poured loosely into a bed sufficient to provide an effective zeolite crystal mass loading within the bed of at least 52 g/100 cc.

18. The method of claim 17 wherein the silica binder is colloidal silica, silicic acid, alkali metal silicate or combinations thereof.

19. The method of claim 17 wherein the silica binder is in an aqueous slurry, wherein the pH of the aqueous slurry of silica binder is adjusted to a pH of 8 or less prior to mixing with the zeolite powder.

20. The method of claim 17 wherein the zeolite powder and silica binder are mixed below incipient wetness.

21. The method of claim 17 wherein the adsorbent particles are formed by agglomeration and compaction, wherein the adsorbent particles are in the form of beads or pellets.

22. The method of claim 17 wherein the adsorbent particles when poured loosely in a bed have an effective zeolite crystal volume loading with the bed of at least 36 g/100 cc, and/or wherein the adsorbent particles have an average crush strength ranging from about 2 to about 8 lbf, and/or the particles have bulk density of at least about 0.5 glee, and/or the particles have an Attrition Index of less than about 0.15, as measured by the SUT Attrition test.

23. The method of any one of claim 17 wherein the zeolite, binder and water is mixed with a high intensity mixer.

* * * * *